(12) United States Patent
Prakash et al.

(10) Patent No.: US 8,764,676 B2
(45) Date of Patent: Jul. 1, 2014

(54) SIGNAL PROCESSING IN PHYSIOLOGICAL NOISE

(75) Inventors: Srinivasamurthy Ravi Prakash, Arlington, MA (US); John J. Guinan, Jr., Newton, MA (US); Barbara Herrmann, Walpole, MA (US); Steven D. Rauch, Watertown, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 952 days.

(21) Appl. No.: 12/776,272

(22) Filed: May 7, 2010

(65) Prior Publication Data

US 2010/0292606 A1 Nov. 18, 2010

Related U.S. Application Data

(60) Provisional application No. 61/176,384, filed on May 7, 2009.

(51) Int. Cl.
*A61B 5/05* (2006.01)

(52) U.S. Cl.
USPC .......................................... 600/554; 600/558

(58) Field of Classification Search
USPC ....................................................... 600/554
See application file for complete search history.

(56) References Cited

U.S. PATENT DOCUMENTS

| | | | |
|---|---|---|---|
| 4,926,969 A | 5/1990 | Wright et al. | |
| 6,415,185 B1 * | 7/2002 | Maltan | 607/57 |
| 2003/0093006 A1 | 5/2003 | Wells et al. | |
| 2003/0149350 A1 | 8/2003 | Porciatti | |
| 2004/0082975 A1 * | 4/2004 | Meyer et al. | 607/27 |

OTHER PUBLICATIONS

Ghorab et al. "Vestibular evoked myogenic potentials: non invasive test of vestibular function" p. 415-421, Egypt J Nurol. Psychiat. Neurosurg. 2004.*
Karp, S. et al.; *"Communication Theory for the Free-Space Optical Channel"*; Proceedings of the IEEE, vol. 58, No. 10, p. 1611-1626, Oct. 1970.
Sharma, K.K et al..; *"Asymptotic Sampling Distribution of Inverse Coefficient-of-Variation and Its Applications"*; IEEE Transactions on Reliability, vol. 43, No. 4, p. 630-633, Dec. 1994.
Dong, G. et al.; *"Intravital Leukocyte Detection Using the Gradient Inverse Coefficient of Variation"*; IEEE Transactions on Medical Imaging, vol. 24, No. 7, p. 910-924, Jul. 2005.

(Continued)

*Primary Examiner* — Max Hindenburg
*Assistant Examiner* — Renee Danega
(74) *Attorney, Agent, or Firm* — Fish & Richardson P.C.

(57) ABSTRACT

The invention relates to systems and methods for estimating a response of at least a part of a physiological system to a first deterministic stimulus signal. The methods include separating a measured first signal into a plurality of segments, each segment representing a response of the physiological system to a corresponding portion of the first stimulus signal and generating a template signal representing the plurality of segments. The methods further include calculating a measure of similarity of each segment in the plurality of segments to the template signal to provide a set of scalar quantities, and determining a metric representing a characteristic of the response of at least a part of the physiological system to the first stimulus signal.

43 Claims, 9 Drawing Sheets

(56) References Cited

OTHER PUBLICATIONS

Prakash, Srinivasamurthy Ravi, *"Vestibular Evoked Myogenic Potentials: Physiology, Variability, and Statistical Characteristics"*; Ph.D Dissertation submitted to the Harvard-MIT Division of Health Science and Technology, MIT, Jun. 2009. 145 pages.

Kutoyants, Y.; Université du Maine, Le Mans, France; *"On Regularity Conditions and Properties of Estimators for Poisson Processes"*; PAMMP, Tsaghkadzor, Sep. 13, 2009. 38 pages.

International Search Report & Written Opinion, Patent Cooperation Treaty, PCT application No. PCT/US2010/034123, mailed Dec. 17, 2010. 8 pages.

* cited by examiner

SIGNAL PROCESSING IN PHYSIOLOGICAL NOISE

CROSS-REFERENCE TO RELATED APPLICATIONS

This application claims the benefit of priority from U.S. Provisional Application Ser. No. 61/176,384, filed on May 7, 2009, the contents of which is incorporated herein by reference in its entirety.

FIELD OF THE INVENTION

The invention relates to detecting characteristics of a signal in the presence of random physiological noise.

BACKGROUND OF THE INVENTION

Electrical signals recorded or measured from a living subject are often used as predictors and/or indicators of the state of a physiological system. In some cases, such signals are recorded to measure the response of the subject to another stimulus signal. For example, vestibular evoked myogenic potentials (VEMPs) are electrical signals recorded from the skin overlying skeletal muscles of the head and neck in response to high-intensity acoustic stimuli. Such signals, however, are characterized by a high degree of variability that depends on various factors including when and where on the skin the signal is being measured and the condition of the subject. The measured signals are also affected by noise from other physiological processes. Thus, signals measured from a living body generally cannot be used as a reliable indicator of a physiological process.

SUMMARY OF THE INVENTION

A physiological system in a live subject can be evaluated by measuring the response of the physiological system to one or more internal or external stimulus signals. In some cases, the response may be measurable only at a distance from the physiological system of interest. The measured signals are affected by random physiological noise and usually exhibit a high degree of variability due to various factors. The present invention is based, at least in part, on the discovery that in some physiological systems, the concomitant physiological noise may be non-additive and the measured signal has to be processed accordingly to glean meaningful information about the physiological process or system of interest.

In one aspect, the invention features methods for estimating a response of at least a part of a physiological system to a first deterministic stimulus signal. These methods include receiving, at a computing device, a first signal measured from the physiological system in response to the first stimulus signal. The methods also include separating, using a processor, the measured first signal into a plurality of segments, each segment representing a response of the physiological system to a corresponding portion of the first stimulus signal and generating, using a processor, a template signal representing the plurality of segments. The methods further include calculating, using a processor, a measure of similarity of each segment in the plurality of segments to the template signal to provide a set of scalar quantities, and determining, using a processor, a metric representing a characteristic of the response of at least a part of the physiological system to the first stimulus signal. The metric is determined based on one or more statistical measures computed from the set of scalar quantities.

In another aspect, the invention features systems for estimating a response of at least a part of a physiological system to a first stimulus signal. These systems include a processor and a device for measuring a first signal. For example, the device can include one or more electrodes. The processor separates the first signal into a plurality of segments, each segment representing a response of the physiological system to a corresponding portion of the first stimulus signal. The first signal is measured from the physiological system in response to the first stimulus signal. The processor further generates a template signal representing the plurality of segments, calculates a measure of similarity of each segment in the plurality of segments to the template signal to provide a set of scalar quantities, and determines a metric representing a characteristic of the response of at least a part of the physiological system to the first stimulus signal. The metric is determined based on one or more statistical measures computed from the set of scalar quantities.

In another aspect, the invention features a computer-readable medium storing a computer program for estimating a response of at least a part of a physiological system to a first deterministic stimulus signal. The computer program includes instructions for causing a computer system to receive a first signal measured from the physiological system in response to the first stimulus signal. The computer program further includes instructions for causing a computer system to separate the measured first signal into a plurality of segments, each segment representing a response of the physiological system to a corresponding portion of the first stimulus signal and generate a template signal representing the plurality of segments. The computer program further includes instructions for causing a computer system to calculate a measure of similarity of each segment in the plurality of segments to the template signal to provide a set of scalar quantities and determine a metric representing a characteristic of the response of at least a part of the physiological system to the first stimulus signal. The metric is determined based on one or more statistical measures computed from the set of scalar quantities.

Implementations may include one or more of the following.

The first signal can be measured from the physiological system using one or more electrodes. Each segment in the plurality of segments can be substantially equal in duration to the other segments. Each segment can be substantially equal in length to a corresponding portion of the stimulus signal. The template signal can be generated by averaging the segments.

The methods can further include receiving, at a computing device, a second signal measured from the physiological system in response to a second deterministic stimulus signal, an intensity of which is greater than the intensity of the first stimulus signal. The methods can further include separating, using a processor, the measured second signal into a plurality of segments, each segment representing a response of the physiological system to a corresponding portion of the second stimulus signal, and generating the template signal based on the plurality of segments from the second measured signal. The second signal can be measured under substantially the same measurement conditions as for the first signal.

The methods can further include receiving, at a computing device, a plurality of third signals measured from a plurality of physiological systems of substantially same type in a population of subjects in response to a third deterministic stimulus signal. The methods can also include separating, using a processor, each of the plurality of third signals into a plurality of segments, each segment representing a response of the corresponding physiological system to a corresponding portion of the third stimulus signal, and generating the template signal based on the segments from the plurality of third signals. The plurality of third signals can each be measured under substantially the same measurement conditions as for the first signal.

In certain embodiments the template signal can be calculated based on one or more parameters of a theoretical model of the physiological system, and calculating a measure of similarity of each segment to the template signal can include calculating a correlation between the segment and the template signal. In some embodiments, the set of scalar quantities can include a correlation coefficient, an inner product, a sum of squared differences (SSD), a root mean squared difference (RMSD), a sum of absolute differences (SAD), and mutual information. The statistical measures computed from the set of scalar quantities can include a measure of central tendency and a measure of dispersion of the set of scalar quantities. The measure of central tendency can be a mean and the measure of dispersion can be a standard deviation. The metric can be a ratio of the mean and the standard deviation.

In certain embodiments, the physiological system can be a vestibular system and the first signal can be a vestibular evoked myogenic potential (VEMP). The stimulus signal can be an acoustic signal. The methods can further include providing instructions to a subject to control a body part of the subject in accordance with the stimulus signal, wherein the physiological system is a part of the subject. The stimulus signal can be one or more of an acoustic signal, an electrical signal, a visual signal, and a mechanical signal. The first signal can be measured in the presence of a random process and the response of at least a part of the physiological system to the stimulus signal can modulate the random process. The response of at least a part of the vestibular system to the acoustic signal can inhibit a spiking activity of a muscle and a level of the spiking activity can be represented by the characteristic. The first signal can be measured in the presence of concomitant physiological noise and the response of at least a part of the vestibular system to the acoustic signal can modulate the physiological noise. The extent of the modulation can depend on the level of spiking activity.

The methods can also include applying the first, second, or the plurality of third stimulus signals to the physiological system. The system can include an audio device for providing the stimulus as an acoustic signal, wherein the physiological system is a vestibular system and the first signal is a vestibular evoked myogenic potential (VEMP).

The invention provides numerous benefits and advantages (some of which may be achieved only in some of its various aspects and implementations) including the following. In general, the invention improves the evaluation of a signal of interest in the presence of non-additive physiological noise by using a statistic that is robust to such noise as well as unwanted variability. For example, the invention can significantly reduce inter-subject and inter-session variability in measuring and evaluating signals of interest, such as, for example, a vestibular evoked myogenic potential (VEMP) in the presence of physiological noise. In addition, the new methods can be used to evaluate other signals, for example, signals that are generated by modulating a physiological random process where the amount or depth of modulation is a parameter of interest. As a result, electrical signals measured from a living subject can be used by physicians for evaluation and diagnosis with increased reliability.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The inventions described herein can be implemented in many ways. Some useful implementations are described below. The descriptions of implementations of the inventions are not descriptions of the inventions, which are not limited to the detailed implementations described in this section, but are described in broader terms in the claims.

Evaluation of Physiological Systems

Figure 1:
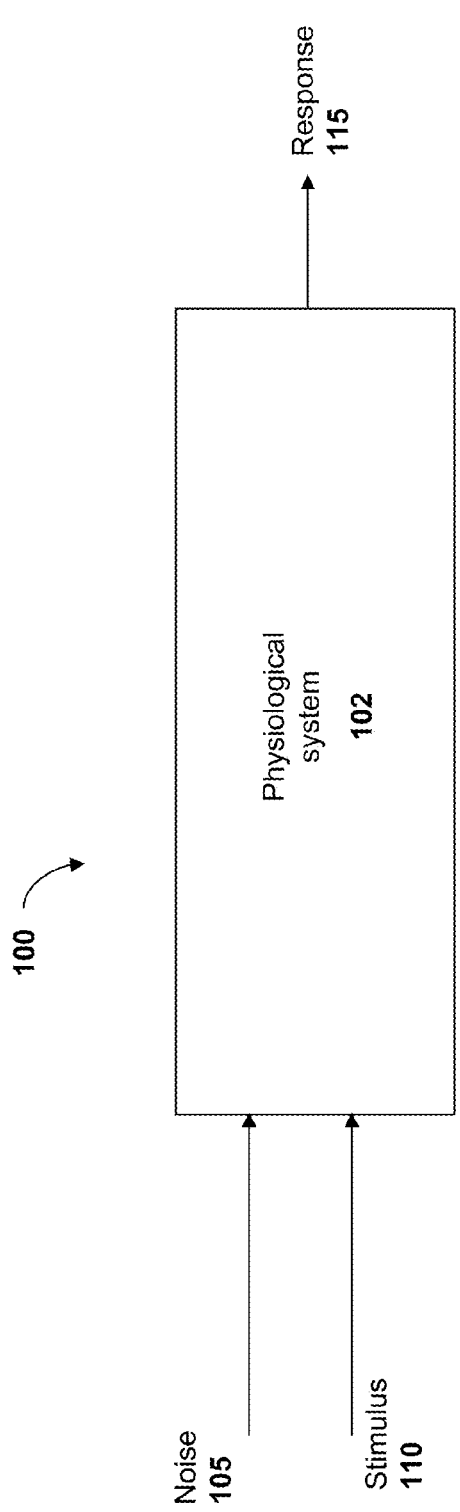
FIG. 1 is a schematic block diagram of a system for evaluating a physiological system.

FIG. 1A shows a system 100 for evaluating a physiological system 102 within a living body. In a typical situation, a stimulus signal 110 elicits an internal response from the physiological system 102. In some cases, the internal response (or the response of the physiological system 102 to the stimulus 110 alone) is a measure of the sensitivity of the physiological system 102, and is therefore a quantity of interest. Often, the internal response cannot be directly measured and is estimated from an overall response 115, which can include other signals, for example, the response of the physiological system 102 to noise 105. In some cases, the quantity of interest is the response of a part of the physiological system 102 while the overall response 115 embodies the response of the entire physiological system 102. The noise 105 can include noise due to various random, non-random and pseudo-random processes inside or external to the living body. In some cases, the internal response modulates one or more parameters of the noise 105. In such cases, the internal response can be evaluated by estimating the amount of such modulation from the overall response 115.

In general, the physiological system 102 can be any combination of parts from the living body. For example, the physiological system can be an organ such as the heart, lungs, liver, or individual muscles. In some cases, the physiological system 102 can include a network of organs such as the digestive system, excretory system, musculo-skeletal system or the vestibular system. The physiological system 102 can also be a part of a system, for example, the peripheral vestibular system.

The stimulus 110 can be of various types. In some implementations, the stimulus is an externally applied signal including, for example, an electrical signal, an acoustic signal, a mechanical signal (e.g., vibration), or any combination thereof. In some implementations, a signal emanating from the living body itself may be used as the stimulus 110. Examples of such internal stimuli include, without limitation, heartbeats, signals representing respiratory cycles, cervical contractions during labor, and muscle tremors. In general, any signal, the variations of which are at least approximately deterministic, and that elicits a response from the physiological system 102, can be used as the stimulus signal 110.

The noise 105 is a combination of signals that affects the physiological system 102. The noise 105 can include, for example, signals arising due to various random, non-random or pseudo random processes going on in a living body, noise emanating from sources external to a living body, or a combination thereof. In some cases, the noise 105 can include the response of other parts of a living body (i.e., external to the physiological system 102) to the stimulus signal 110. For example, if the physiological system of interest 102 is the heart and the stimulus 110 is a series of electrical pulses applied to the heart, a response of the musculo-skeletal system to the electrical pulses would be a part of the noise 105.

In some cases, the overall response 115 is measured at a location remote to the physiological system 102. For example, the physiological system 102 of interest can be a network of skeletal muscles while the overall response 115 is measured at the skin surface overlying such muscles.

Modeling a Physiological System

Figure 2:
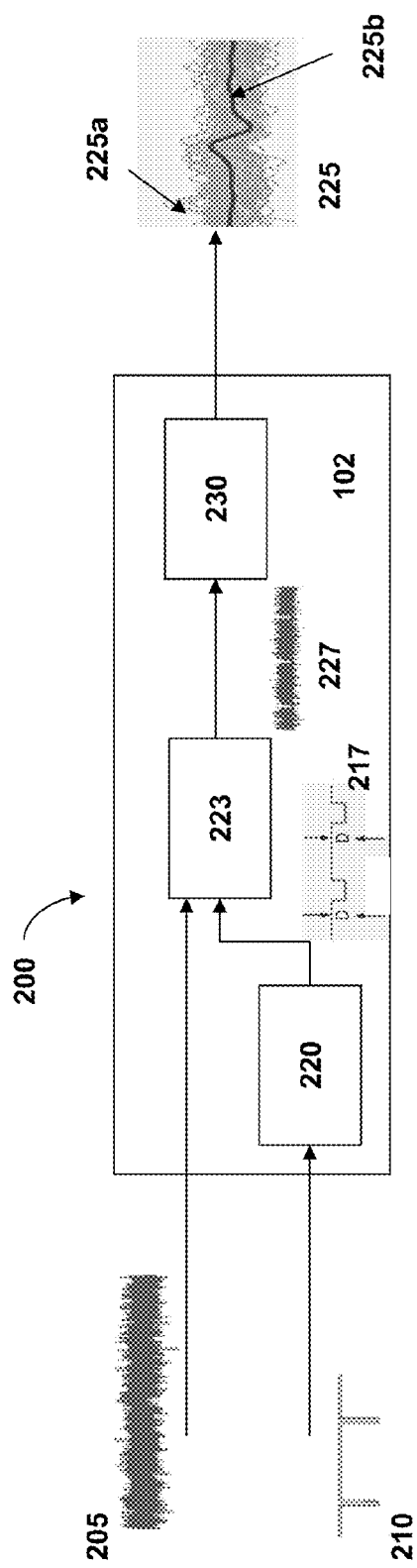
FIG. 2 is a schematic diagram of a model representing a physiological system where the noise is non-additive.

FIG. 2 illustrates an exemplary mathematical model 200 of the physiological system 102. In this model, an organ or other part of interest within the physiological system 102 is represented as a module 220 that produces a response 217 when stimulated with a stimulus signal 210. The signal 217 is the modulating signal that modulates the noise 205 arising, for example from a random process. In some cases, the noise 205 can be modeled as a point process. The signal 217 represents the internal response of the physiological system or organ 220 to the stimulus signal 210. The internal response can be characterized by a parameter of the signal 217, for example, a depth of modulation (also referred to as inhibition depth) "D." In this model, a module 223 modulates the noise 205 with the signal 217 resulting in the modulated signal 227. The signal 225 is a response signal measured or otherwise derived from one or more measurements.

In this example, an average response 225b is derived from multiple measured traces or segments 225a corresponding to a particular segment (for example, a single pulse) of the signal 210. A filter 230 models the transformation of the modulated signal 227 prior to measurement. For example, if the organ of interest 220 is a muscle while the measurement is taken on the skin surface, the filter 230 represents the transformation of the modulated signal between the muscle and the skin surface. In some cases, the measurement system (for example hardware such as electrodes) also introduces certain changes in the measured signal. In the model shown in this example, such changes or transformations (for example, frequency selective filtering) can also be accounted for with the filter 220. In some implementations, the response signal can include additive noise that arises due to various factors including, for example, due to instrument sources as well as the electrical activity of muscles and nerves unrelated to the physiological system of interest.

Variations in Measured Physiological Signals

Figure 3:
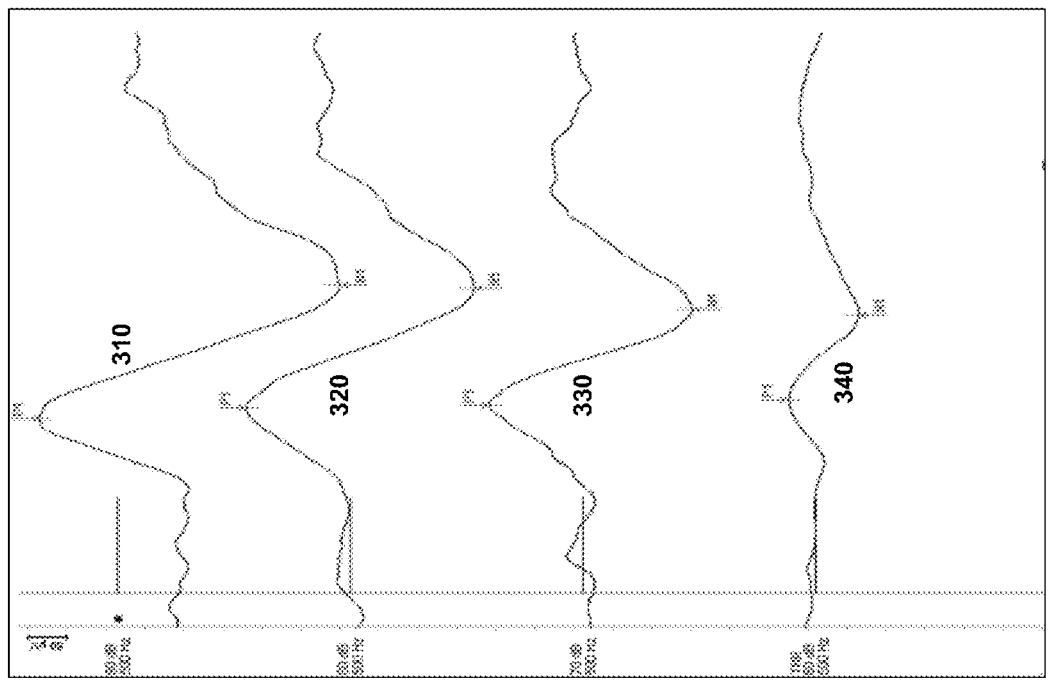
FIGS. 3 and 4A-E are plots illustrating exemplary variations in a physiological signal.
Figure 4:
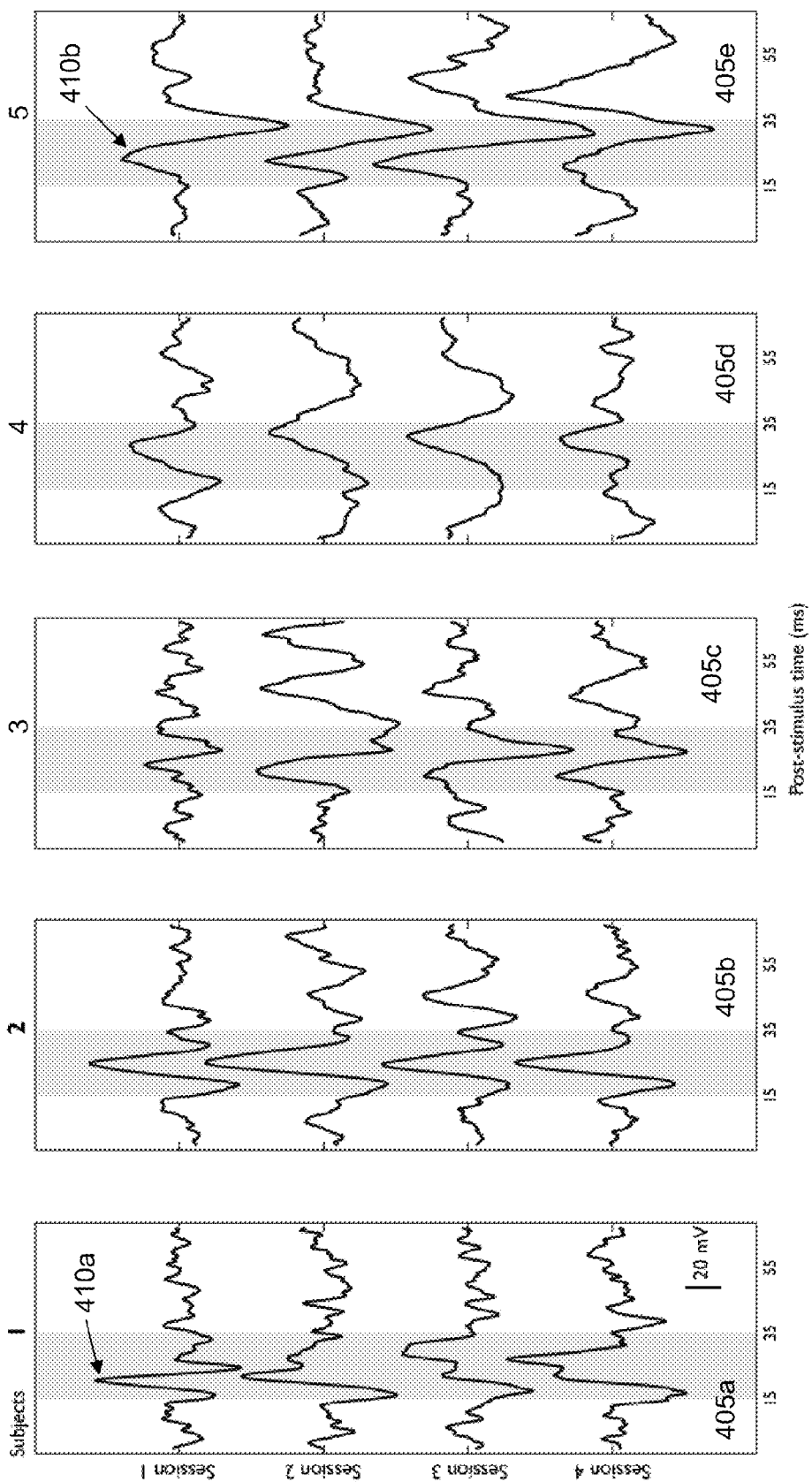

In some implementations, a characteristic or parameter of the measured signal 225 changes in accordance with a parameter of the stimulus signal 210. For example, a change in amplitude of the stimulus signal can affect, for example, a peak-to-peak swing of the measured signal 225. This is illustrated in FIG. 3 by way of an example. FIG. 3 shows a plot 300 that illustrates exemplary variations in a measured signal as a function of the amplitude of a stimulus signal. The waveforms shown in this example are electrical signals recorded from the skin overlying skeletal muscles of the head and neck in response to high-intensity acoustic stimuli. Such electrical signals are also known as vestibular evoked myogenic potential (VEMP).

The purpose of the VEMP test is to determine if the saccule, an otolith organ of the vestibular system of the inner ear, as well as the inferior vestibular nerve and central connections, in the inner ear are intact and working normally. The saccule has a slight sound sensitivity that is exploited in a VEMP test. Each VEMP waveform represents the averaged electromyogram (EMG) signal at different time points relative to a spike in the acoustic stimulus signal, and is computed by averaging the individual post-stimulus EMG signals. The waveforms shown in the example in FIG. 3 represent the average of a number of traces of VEMP measurements from stimulation of one ear. In this example, acoustic signals of frequency 500 Hz and duration 8 ms are used as the stimuli. The intensity of the acoustic signal is varied while keeping the other parameters unchanged. The waveform 310 represents a VEMP signal when the stimulus intensity is 90 dB. The waveforms 320, 330, and 340 represent VEMP signals when the stimulus intensity are 80 dB, 70 dB, and 60 dB, respectively.

In each waveform, P1 represents the peak positive signal value whereas N1 represents the peak negative signal value. From the waveform 310, it is observed that for 90 dB stimulus intensity, the difference between P1 and N1 is about 400 µV. The difference is seen to reduce with reducing stimulus intensity and from waveform 340, it is seen that the difference is about 100 µV for a stimulus intensity of 60 dB. Such experimentation with a large number of subjects with known vestibular conditions yields an understanding of how to interpret the measured signals to assess unknown vestibular conditions. FIG. 3 shows the VEMP signal as an example of how a characteristic of a measured signal can be used in conjunction with a stimulus to assess unknown conditions. In that respect, FIG. 3 should not be considered limiting and it should be noted that other signals measured at various parts of a living body are also within the scope of this application.

Physiological signals measured from a living body are in general subject to large variations even when measured under substantially similar conditions. This is illustrated in FIGS. 4A-E by continuing with the example of VEMP. During VEMP testing, a subject is usually instructed to contract certain muscles as they hear the acoustic stimuli. Otolith reflexes interact with the motor drive to a contracted muscle to give rise to the VEMP signal. The measured signal is therefore dependent on the amount of effort a subject can put into contracting the muscles. The measurements are therefore different for different subjects, because the ability to contract the muscles can vary from one subject to another due to reasons such as differences in size, age and physical ability. Even for the same subject, the ability to contract muscles can vary from one session to another (or even within the same session) due to, for example, muscle fatigue. Examples of such variations are illustrated in FIGS. 4A-E.

In this example, the average of the ensemble of various traces from one recording at 90 dB stimulus level is shown in the plots 405a-405e for five different subjects in four different session. It is noted from FIGS. 4A-E that there is considerable inter-subject variation in the morphology and the salient features (amplitude, peak latencies, etc.) of the averaged measured signals, even though the measurements were obtained under substantially similar conditions. For example, the amplitude of the peak 410a for subject 1 is seen to be much higher than the corresponding peak 410b of subject 5. Even for the same subject, the variations from one session to another are observed to be significant. For example, plot 405e shows large inter-session differences in all waveform features for subject 6. On the other hand, plot 405b shows that the inter-session variability for subject 2 is less pronounced.

In some cases, intra-session variability may also be seen. The intra-session variability or differences can be attributed to causes such as intrinsic noise that remains even after averaging and variations in muscle contraction efforts through the session. The inter-session variability can be attributed to, for example, differences in muscle activation between contractions, fatigue level and difference in locations of electrode placement. The inter-subject variability can be attributed to factors such as age, sex, physical ability and other vestibular and non-vestibular factors such as muscle architecture. The relationship of the noise to the inter-session variability and to inter-subject differences is therefore of interest. Even though VEMP signals are used in this example, it should be noted that other measured physiological signals are also subject to similar intra-session, inter-session, inter-subject or other forms of variability and are within the scope of this application.

Signal Processing

Figure 5:
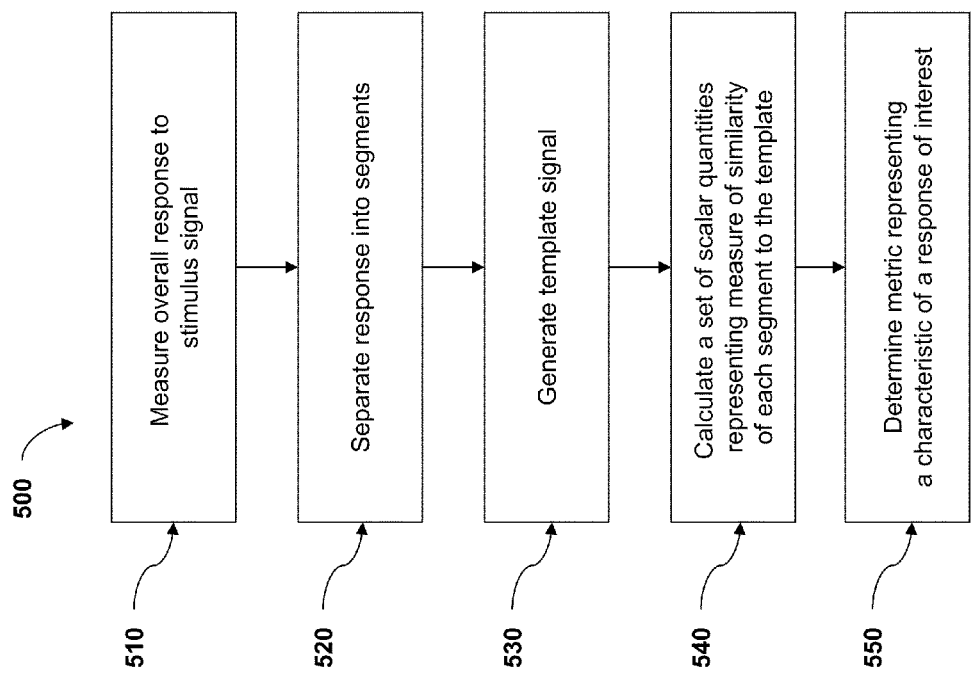
FIG. 5 is a flow diagram depicting an exemplary sequence of operations for analyzing physiological signals.
Figure 6:
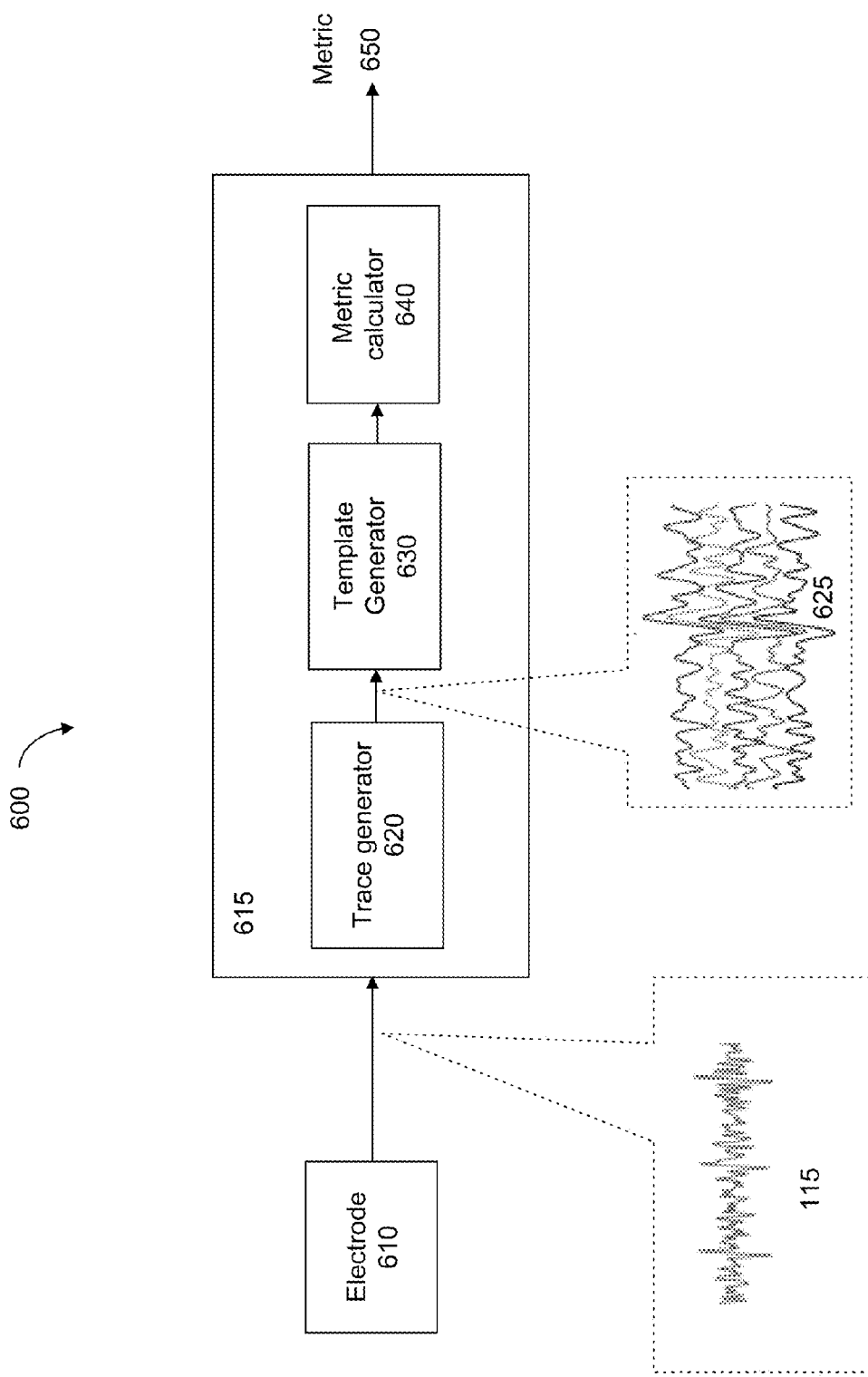
FIG. 6 is a schematic block diagram of a system for analyzing physiological signals.

Referring now to FIG. 5, a flowchart 500 depicts exemplary operations for analyzing and processing signals measured from a physiological system or other parts of a living body. Operations include measuring an overall response (step 510) of a physiological system or organ of interest to a stimulus signal. Referring also to FIG. 6, a system 600 includes one or more electrodes 610 to measure such response. The measurements can be taken by placing electrodes 610 or other sensors at or near the physiological system of interest. In some implementations, the response of the system of interest is manifested at a first location, remote to the system of interest, and the measurements are done at a second location also remote to the system of interest. For example, in VEMP testing, the physiological system of interest is a part of the vestibular system. The response of the system of interest to the stimulus, in case of VEMP, is manifested in a network of skeletal muscles of the head and neck whereas the response is measured using electrodes placed at skin surface overlying the network of the skeletal muscles of the head and neck. In such cases, the overall response is a processed version of the response of the system of interest. A characteristic of the response of the system of interest is then derived by processing the measured overall response appropriately.

The stimulus signal can be of various type and forms. For example, the stimulus signal can include acoustic, visual, electrical and mechanical signals or any combination thereof. In general, the stimulus signal evokes a response from the physiological system of interest and the response or some modified version of the response is measured (step 510) using an appropriate detector or sensor 610.

Referring again to FIG. 5, operations further include separating the response (step 520) into various segments or traces.

In general, physiological response signals exhibit significant variations and hence a large number of measurements under substantially similar conditions are recorded. Such multiple measurements are often referred to as traces. The resulting set of traces or segments are often collectively referred to as an ensemble. In some implementations, the stimulus signal is applied to the physiological system of interest multiple times and the corresponding responses are measured. For example, the stimulus signal can be a periodic or aperiodic train of pulses. In some implementations, the timing information of the pulses is used to separate the measured signals into different segments or traces. In general, the overall response is separated into segments such that each segment represents the response to a corresponding segment of the stimulus signal. Where the stimulus signal is periodic, the segments can be of substantially equal length with each segment corresponding to a particular period of the stimulus signal. In some implementations, some predetermined information may be used in separating the response into different segments. For example, a latency between the application of stimulus and recording the corresponding evoked response may be predetermined under known test conditions and parameters.

The operation of separating the response (step 520) into different traces can be performed using a processor in a computing device 615 as shown in FIG. 6. In some implementations, the computing device 615 can include a trace generator module 620 to separate the measured response 115 into an ensemble 625 of traces or segments. The trace generator module 620 may be a hardwired unit or can be implemented using a processor in the computing device 615 by executing instructions encoded in computer readable language stored on computer readable storage media. For example, in some implementations, the trace generator module 620 can be implemented using a software package such as MATLAB®.

In general, the trace generator 620 segments the incoming signal 115 into multiple parts based on the stimulus signal. For example, in some implementations, the trace generator 620 parses the stimulus signal into individual segments, for example by zero crossings. The trace generator can use the information on stimulus positions to segment the incoming signal 115. In some implementations, multiple traces corresponding to the stimuli are saved by the trace generator 620 in a file as a two dimensional array of numbers. The trace generator 620 may communicate with a database or other storage media to store such files.

Referring back to FIG. 5, operations also include generating (step 530) a template signal from the ensemble of traces or segments. In general, the template signal is a representative curve for a given ensemble of traces. In some implementations, the template signal is normalized such that the sum of the mean squared values of the data points equals unity. The template signal can be generated in a variety of ways. In some implementations, values corresponding to a same time point in different segments can be averaged to generate the template signal. The averaging can be simple averaging or a weighted averaging with respect to some parameter.

In some implementations, the template signal for a given ensemble of traces can be generated from another ensemble of traces recorded under substantially the same measurement conditions.

In some implementations, the template signal can be generated by estimating a representative response from responses recorded from a substantially large population of subjects. Multiple recordings may be taken for each of the subjects in calculating the representative response. In some cases, multiple template signals can be generated for different groups of population. For example, one template can be generated for an age group of 30-40 using a suitable population of subjects while another template can be similarly generated for an age group between 60-70. In general, various template signals can be generated for different groups and sub-groups by selecting the population of subjects accordingly. Some of the parameters that can be considered for generating multiple templates include, but are not limited to, physical characteristics such as height, weight or body mass index, disability, age, or any other parameter that might affect the measured response of the physiological system of interest.

In some implementations, the template signal can be calculated using theoretical analysis. For example, a physiological system can be modeled mathematically and the response of the physiological system to a deterministic stimulus signal can be calculated from a theoretical point of view. Such theoretical computations can be used to generate an expected response waveform taking into consideration various real factors as parameters in the theoretical model. In some cases, a validity of the theoretical model may be pre-established using experimental data.

In some implementations, more than one approaches of generating the template signal can be used in conjunction with each other. For example, a template can be calculated for a given ensemble of a given population using traces from a separate ensemble for the same population. Continuing with the above example, the template can in turn be generated by averaging the traces from the separate ensemble.

Referring again to FIG. 6, the template signal can be generated using a template generator module 630. The template generator module 630 can be a hardwired unit or can be implemented using a processor in the computing device 615 by executing instructions encoded in computer readable language stored on computer readable storage media. The template generator 630 may interface with one or more databases to retrieve data such as information on pre-recorded traces, recorded, for example, by the trace generator 620. In some implementations, the template generator 630 can be implemented using a software package such as MATLAB®. When the traces are stored in computer readable files, for example as two-dimensional arrays, the template generator 630 can generate the template from such files. For example, if each trace is saved in the array as a separate row, the template generator 630 can compute the average of each column to produce a row of values that represents the template signal. Similarly, the template generator may use the data stored in such files in other ways to compute the template signal. In some implementations, the template generator uses parameters from a theoretical model to compute the template signal.

Referring back to FIG. 5, operations also include calculating (step 540) a measure of similarity of each segment within an ensemble to the generated template signal. In general, the measure of similarity is a scalar quantity that represents a degree of similarity of a given trace with the template waveform. The measure of similarity can include, without limitation, a correlation, correlation coefficient, inner product, sum of squared differences (SSD), root mean squared difference (RMSD), sum of absolute differences (SAD) and information theory based measures such as mutual information. The above measures of similarity can be mathematically calculated and describe the degree of relationship between the sets of data representing a trace and the template signal. For example, the SSD can be calculated by computing the difference of each number in a given set from the corresponding number in the other set, and summing the square of the differences. Similarly, SAD, can be calculated by summing the absolute differences between the corresponding data points in the two sets. Mutual information is a measure that can be calculated based on the probability distribution of the data points in the two data sets, respectively. In some cases the traces within an ensemble are unequal in length and the template in general can be of a length different than that of a given trace. In such cases, a data set representing a trace may have to be appropriately padded, for example with zeros, prior to calculating the measure of similarity, to a length substantially equal to that of the data set representing the template waveform. In some cases, the data set representing the template waveform can also be punctured (i.e., one or more values removed from the data set representing the template waveform) or cropped such that the template data set is substantially equal in length to the trace data set. In general, step 540 yields a number of scalar quantities substantially equal to the number of traces in a given ensemble.

Operations also include determining (step 550) a metric from the set of scalar quantities such that the determined metric represents a characteristic of the response of the organ of interest. In some implementations, determining the metric includes computing a measure of central tendency from the set of calculated scalar quantities. Such measure of central tendency can include, without limitation, arithmetic mean, geometric mean, harmonic mean, truncated mean, weighted mean, mode, median, and percentile. Determining the metric can also include computing a measure of dispersion such as variance, standard deviation, interquartile range, range, mean difference, median absolute deviation, average deviation, coefficient of variation, and coefficient of dispersion. Determining the metric can further include calculating a function of two or more measures of central tendency and/or dispersion. For example, in some implementations, determining the metric can include calculating a ratio of a mean of the set of scalar quantities to a standard deviation (or variance) of the set of scalar quantities. This ratio is also referred to as an inverse coefficient of variation (iCov). In some implementations, the iCov, similar to the average of the traces in an ensemble, is approximately proportional to the level of stimulus (or a related characteristic of the response of the organ of interest to the stimulus) but is comparatively more robust to inter-subject and inter-session variations. In some implementations, calculating the metric also includes multiplying a calculated value (for example, iCov) by a scale factor. The scale factor, in general, is application dependent and is calculated based on theoretical considerations and/or computational modeling.

Referring again to FIG. 6, the metric calculator 640 can be used to perform the calculations described herein. For example, the metric calculator 640 can be used to calculate the set of scalar quantities representing the similarity of the traces with the template signal. The metric calculator 640 can also be used to calculate the metric 650 from the set of scalar quantities and optionally multiply the metric by a scale factor.

System Overview

Figure 7:
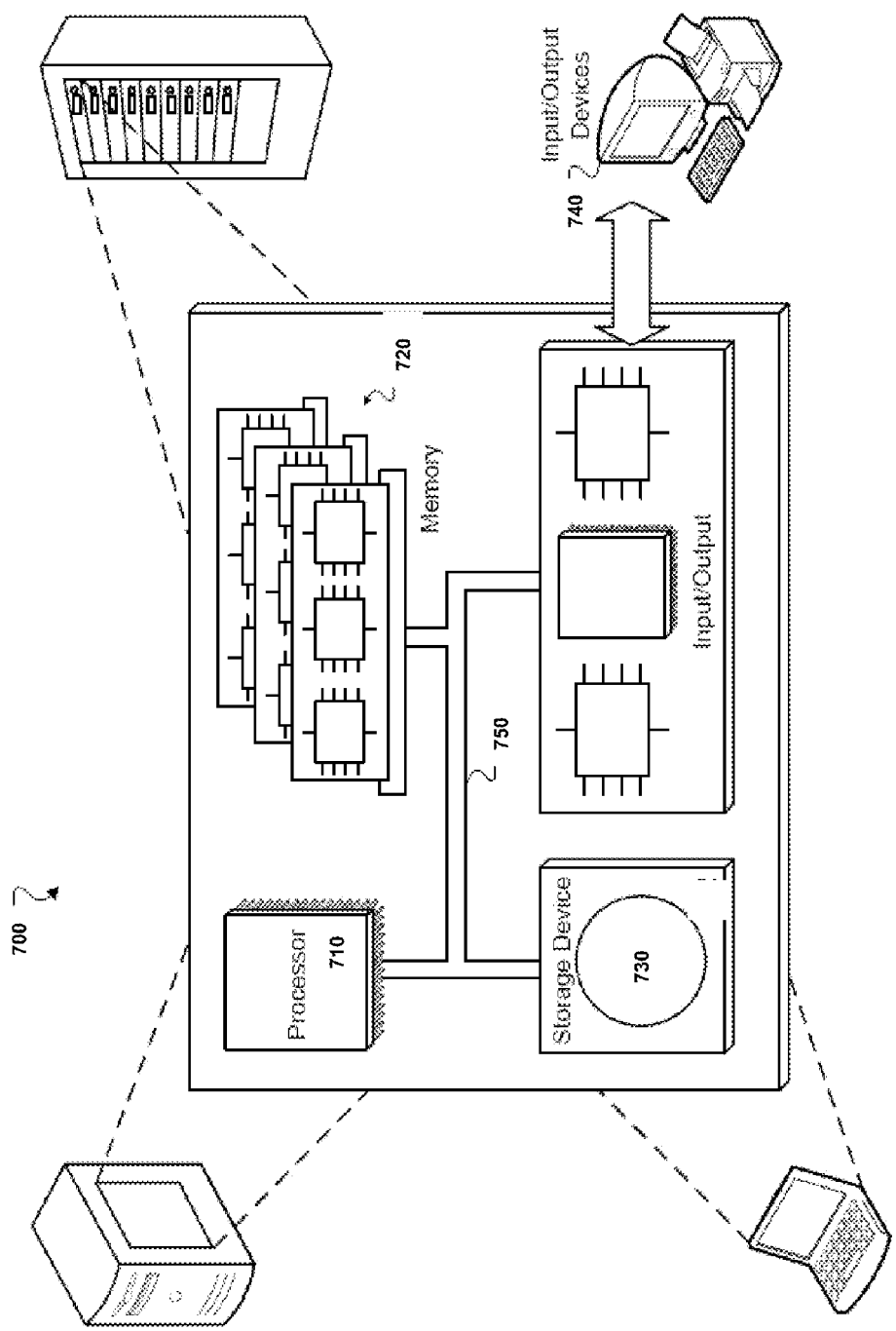
FIG. 7 is a schematic diagram of a computing device and system.

FIG. 7 is a schematic diagram of a computer system 700. The system 700 can be used for the operations described in association with any of the computer-implemented methods described herein, according to one implementation. The system 700 includes a processor 710, a memory 720, a storage device 730, and an input/output device 740. Each of the components 710, 720, 730, and 740 are interconnected using a system bus 750. The processor 710 is capable of processing instructions for execution within the system 700. In one implementation, the processor 710 is a single-threaded processor. In another implementation, the processor 710 is a multi-threaded processor. The processor 710 is capable of processing instructions stored in the memory 720 or on the storage device 730 to display graphical information for a user interface on the input/output device 740.

The memory 720 stores information within the system 700. In some implementations, the memory 720 is a computer-readable medium. The memory 720 can include volatile memory and/or non-volatile memory.

The storage device 730 is capable of providing mass storage for the system 700. In one implementation, the storage device 730 is a computer-readable medium. In various different implementations, the storage device 730 may be a floppy disk device, a hard disk device, an optical disk device, or a tape device.

The input/output device 740 provides input/output operations for the system 700. In some implementations, the input/output device 740 includes a keyboard and/or pointing device. In some implementations, the input/output device 740 includes a display unit for displaying graphical user interfaces.

The features described can be implemented in digital electronic circuitry, or in computer hardware, firmware, or in combinations of them. The features can be implemented in a computer program product tangibly embodied in an information carrier, e.g., in a machine-readable storage device, for execution by a programmable processor; and features can be performed by a programmable processor executing a program of instructions to perform functions of the described implementations by operating on input data and generating output. The described features can be implemented in one or more computer programs that are executable on a programmable system including at least one programmable processor coupled to receive data and instructions from, and to transmit data and instructions to, a data storage system, at least one input device, and at least one output device. A computer program includes a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. Computers include a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

The processor 710 carries out instructions related to a computer program. The processor 710 may include hardware such as logic gates, adders, multipliers and counters. The processor 710 may further include a separate arithmetic logic unit (ALU) that performs arithmetic and logical operations.

EXAMPLE

The invention is further described in the following example, which does not limit the scope of the invention described in the claims.

Analysis of VEMP Signals

Overview

Vestibular Evoked Myogenic Potentials (VEMPs) are electrical signals recorded from the skin overlying skeletal muscles of the head and neck in response to high-intensity acoustic stimuli. VEMP signals originate in the otolith organs of the inner ear, which are vestibular (balance) organs responsible for sensing acceleration and orientation with respect to gravity. Otolith reflexes interact with the motor drive to a contracted muscle to give rise to the VEMP signal. VEMP signals from neck muscles can be used as an indicator of peripheral vestibular function and for assessing the functioning of the saccule and its innervation.

In brief, the saccule has a phasic response to acoustic stimulus comprising spikes or impulses. The saccule response activates an inhibitory reflex from the vestibular nuclei to the sternocleidomastoid (SCM) motoneurons. The inhibitory reflex modulates the ongoing activity of motor units of the SCM muscle under voluntary contraction wherein the ongoing activity of motor units are modeled as a random process. The modulation affects at least one characteristic or statistic of the surface electromyogram (EMG), and changes in the mean of the measured surface EMG constitutes the VEMP response.

Figure 8:
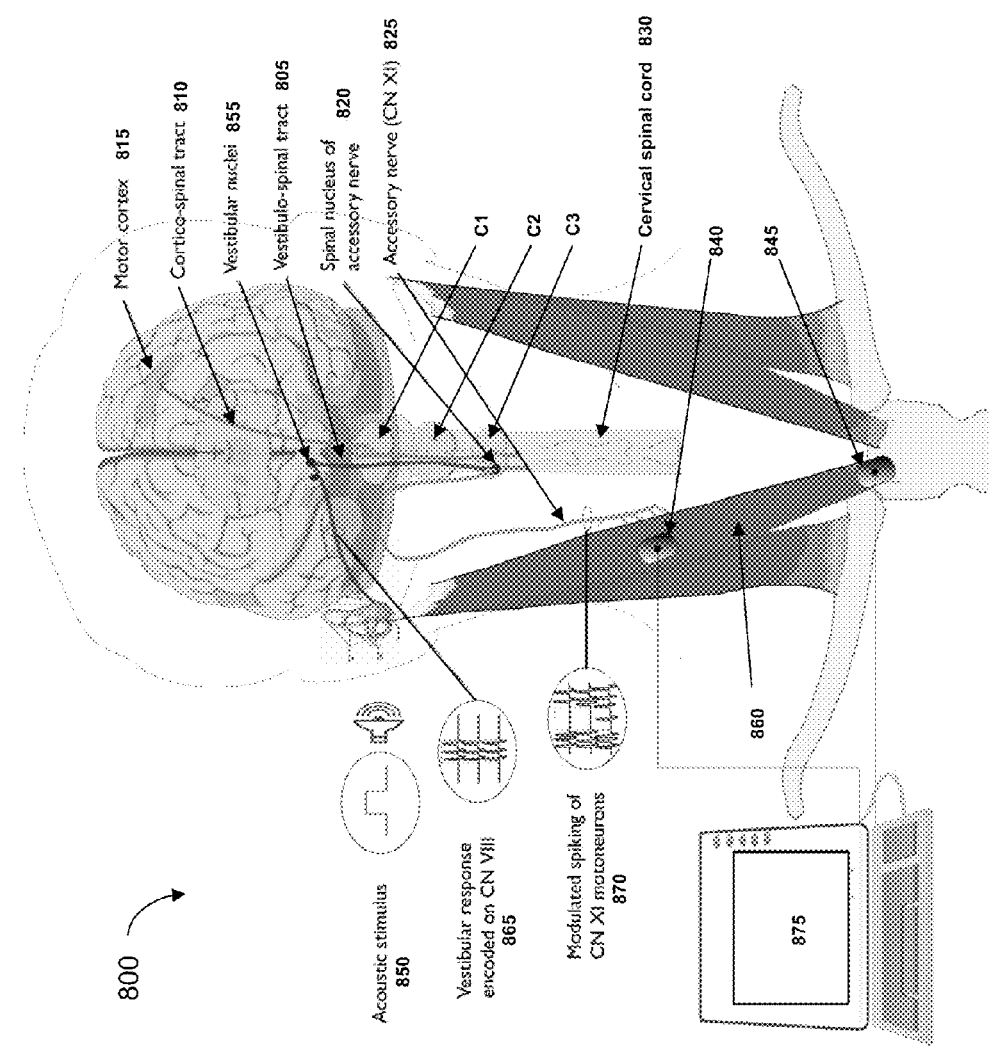
FIG. 8 is a schematic diagram of an exemplary physiological model for measuring a VEMP signal.

Referring now to FIG. 8, a schematic diagram shows an example of the physiology for VEMP measurements along with a model of signal interactions that lead to VEMP reflexes. The interaction between the vestibulo-spinal tract 805 and cortico spinal tract 810 emanating from the motor cortex 815 occurs at the pool of motor neurons of the spinal nucleus 820 of the accessory nerve (CN XI) 825 located in segments C1-C3 of the cervical spinal cord 830. Each motor neuron defines a collection of muscle fibers that it innervates (the motor unit) and each action potential on the motor neuron results in the coordinated firing of action potentials that propagates along each muscle fiber from the innervation zone in the belly of the muscle towards the tendons where the muscle in inserted into the bone.

When no acoustic stimulus is applied and the subject performs a constant-tension isometric contraction of the muscle, and there are no fatigue effects, the motor neuron pool is driven by a constant net motor drive which is the resultant of the cortico-spinal drive and various muscle reflexes.

In response to the firing of an action potential on a spinal accessory motor neuron, the simultaneous depolarization of the muscle fibers of the corresponding motor unit causes a pattern of surface potential changes that are recorded with the two electrodes, 840 and 845 over the belly and tendon of the muscle, respectively. This unit surface response is referred to as the "motor unit action potential response" (MUAPr) of that motor unit. The MUAPr is a single waveform that reflects the combined effect of the time-course of the transmembrane current of the muscle fibers, the properties of the motor unit (for example, the number of fibers, the mean distance of the fibers from the electrode, the fiber diameter and the conduction velocity) and the measurement system (for example, electrode geometry, electrode position and amplifier bandwidth).

With the details of the action potential shape included within the MUAPr, the spiking activity of each motor neuron can be represented simply as a sequence of impulses (Dirac delta functions) at delays corresponding to the position of each motor unit spike. The contribution of a given motor unit to the surface EMG is therefore the convolution of the MUAPr with the spike sequence of the motor neuron, and the surface EMG is the total contribution from all the units. The surface EMG can therefore be modeled as the summed output of a set of filters driven by impulse trains, where the impulse response of each filter is the MUAPr of a particular motor unit.

When an acoustic stimulus 850 is applied to an ear, at least a part of the energy of the stimulus 850 couples into the vestibular system (the saccule in particular) and elicits a burst of activity on the afferent nerve fibers that project on the vestibular nuclei 855. This in turn activates reflex pathways that descend along the vestibulospinal tract 805 to form inhibitory projections on the motor neurons of the accessory nerve 825 ipsilateral to the stimulated ear. As a result, if the activity of a motor unit in a tonically contracted sternocleidomastoid (SCM) muscle is monitored, each stimulus toneburst applied at the ear is found to be followed by a brief period of inhibition of the spiking activity of the unit. Such spiking activity can be characterized by an inhibition depth which is the vestibular response 865 to the acoustic stimulus signal. The time-course of this inhibition is determined by the mechanics of the vestibular periphery and the fidelity of neural encoding on the afferent and the descending pathways.

The effect of inhibition on the motor unit spike sequences, which are characterized by the modulated spiking 870 of the motoneurons, and the resulting changes in surface response are determined by the neurophysiology of the motor neuron, and the superposition of multiple MUAPr waveforms (at different delays) from the motor unit is recorded on a computing device 875 using the electrodes 840 and 845. The averaged surface response from the SCM muscle is recorded as the VEMP signal.

Setup

To measure VEMP signals, surface electrodes were placed on the skin over the sternocleidomastoid (SCM) muscle on one side of the neck. The subject was asked to contract the muscle under test either by turning the head or by lifting the head from a supine position. The subject maintained maximum voluntary tension on the muscle, and was assisted by direct or indirect feedback of the ongoing EMG level. Acoustic stimuli (tonebursts or clicks) of alternating polarity were applied to the ear ipsilateral to the muscle being recorded at a rate of 13 stimuli/sec. The 500 Hz tonebursts used as the stimuli were generated using a Blackman window with a two-cycle rise and fall and no plateau. The stimulus waveform was generated by the clinical VEMP system using NATIONAL INSTRUMENTS 6052-E boards. The analog signal at a fixed level was amplified by a VIRTUAL MODEL 320 audiometer power amplifier, whose gain and attenuation were set to yield the specified stimulus intensity. The stimulus was delivered over TELEPHONICS TDH-49 circumaural headphones.

The surface EMG of the SCM muscle was measured using adhesive surface electrodes (ULTRATRACE® Adult ECG electrodes). The skin surface was cleaned with alcohol, and gently abraded to improve the electrical contact. A single-differential electrode montage was used: active electrode on the muscle belly, reference electrode on the sternal insertion of the muscle and ground on the forehead The electrical signals measured at the surface electrodes were amplified, band-pass filtered, and recorded in synchronization with the stimuli. The electrode outputs were amplified by a TUCKER-DAVIS Bioamp system (TDT-HS4 head stage & TDT-DB4 amplifier). This analog signal was sent to both the clinical VEMP system and the trace recording system. An ensemble of traces was recorded for a subject in a given session. A waveform of running average of the EMG signal over an approximately 50 ms post-stimulus interval was computed and displayed.

In the trace recording system, the stimulus waveform as well as the amplified EMG were simultaneously sampled at 25 kHz and streamed to disk using two National Instruments NI6052-E boards and the custom LABVIEW® VI. The two acquisition boards operated on a common sampling clock to avoid offsets in the stimulus and EMG sampling instants. This clock was free-running, and independent of the clock used in the VEMP system.

The recording was terminated when a stable waveform was obtained or no such response was found. When a trace recording was terminated, a MATLAB® script converted the streamed samples into an array of numbers and saved the array.

The typical output of a VEMP test is a set of waveforms stacked by stimulus intensity such as shown in FIG. 3. Each VEMP waveform represents the averaged EMG at different time points relative to the stimulus, and is computed by averaging the individual post-stimulus EMG signals. In general, VEMP waveforms show a characteristic biphasic pattern with an initial latency of 11-15 ms, and duration of 15-30 ms, and peak-peak amplitudes ranging from about 20 µV to greater than 200 µV depending on the stimulus level and contraction effort of the subject.

Signal Processing

Each recording session produced a series of data files containing stimulus and EMG waveforms. These files were processed off-line using a series of MATLAB scripts. The stimulus recording was parsed into individual stimuli by detecting the zero-crossing at the center of the each toneburst. The identified stimulus positions were used to segment the EMG recording (since the samples of the stimulus and EMG were acquired synchronously) into individual traces each trace being roughly 70 ms (approx. 1700 samples) long. Each contraction at a given stimulus intensity and effort level yielded an array of about 500 EMG traces. The DC offset was subtracted from the EMG signal prior to parsing it, making the signal zero-mean. The resulting 2-dimensional array of EMG traces from each recording was saved into a file that identified the subject number, session number, set number (of the two maximal and one moderate effort contractions), and the stimulus intensity.

For a recorded ensemble of traces for a given subject, a template response was computed from the average of traces obtained at maximum voluntary contraction and maximum stimulus intensity. For every trace in the ensemble, the inner product with the template response was computed to obtain a sequence of real numbers. The iCov for each sequence was computed as a ratio of the mean and the standard deviation. The inhibition depth was calculated from a predetermined relationship between the iCov and the inhibition depth. The relationship between the iCov and the inhibition depth can be calculated in various ways, including using the computational model of VEMP described in: "Vestibular Evoked Myogenic Potentials: Physiology, Variability, and Statistical Characteristics," Ph.D dissertation by S. R. Prakash, Massachusetts Institute of Technology, June 2009, the entire content of which is hereby incorporated by reference.

Figure 9:
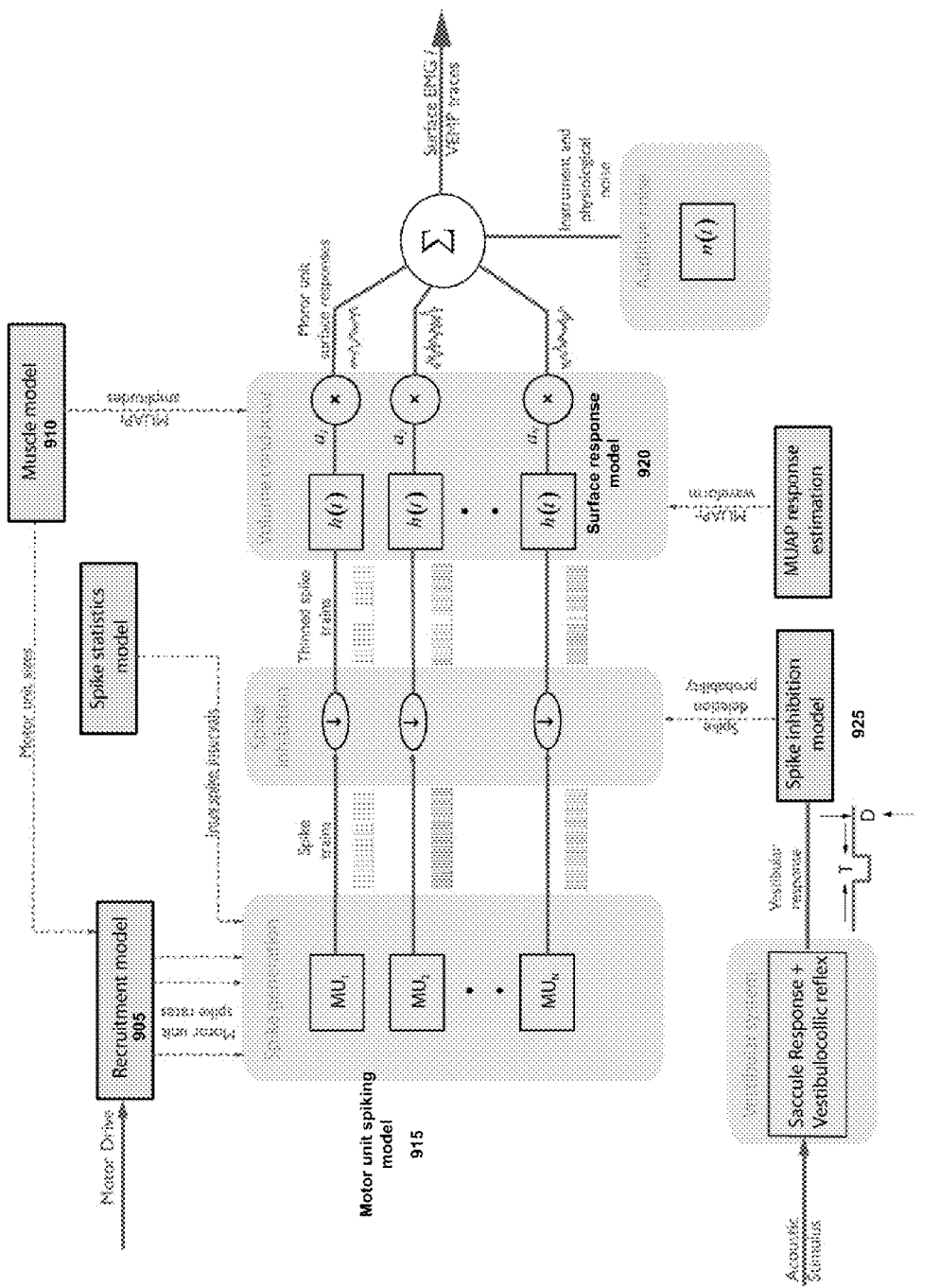
FIG. 9 is a schematic diagram of a model representing a physiological system.

FIG. 9 shows an example of a model that can be used to determine a relationship between the iCov and the inhibition depth. With the appropriate choice of physiologically realistic parameters, the model can produce synthetic VEMP signals or EMGs with the substantially same single-point statistics (i.e., distribution) and time-series statistics (e.g., autocorrelation) as the experimental surface EMG from a given subject/session. With appropriately chosen model parameters, which modulate the motor unit spike rate on every trace, result in a surface EMG ensemble which, when averaged, yields a recognizable VEMP-like waveform. The synthetic VEMP trace ensemble is statistically similar to the experimental VEMP from the same subject/session. Specifically, VEMP sub-averages computed from both experimental and synthetic ensembles of traces show a similar degree of variability. At the same time, if experimental data from two subjects/sessions are statistically dissimilar, the corresponding synthetic data ensembles are also, in general, statistically dissimilar. The synthetic VEMP amplitude and latency parameters show a dependence on stimulus intensity and contraction effort that is substantially similar to experimental data.

As noted, the interaction between the vestibular and motor pathways occurs at the pool of motor neurons of the spinal nucleus of the accessory nerve (CN XI) located in segments C1-C3 of the cervical spinal cord. When no acoustic stimulus is applied and the subject performs a constant-tension isometric contraction of the muscle, and there are no fatigue effects, the motor neuron pool is driven by a constant net motor drive which is the resultant of the cortico-spinal drive and various muscle reflexes. As shown in FIG. 9, the recruitment model 905 maps this net drive into the firing of each motor neuron in the pool.

In response to the firing of an action potential on a spinal accessory motor neuron, the simultaneous depolarization of the muscle fibers of the corresponding motor unit causes the motor unit action potential response (MUAPr) of that motor unit. With the details of the action potential shape included within the MUAPr, the spiking activity of each motor neuron can be represented simply as a sequence of impulses (Dirac delta functions) at delays corresponding to the position of each motor unit spike. The contribution to the surface EMG from a given motor unit is therefore the convolution of the MUAPr with the spike sequence of the motor neuron, and the surface EMG is the summed contribution from all the units. Equivalently, the surface EMG can be treated as the summed output of a set of filters driven by impulse trains, where the impulse response of each filter is the MUAPr of a particular motor unit.

In the computational model shown in FIG. 9, a number of assumptions can be made. For example, it is assumed that the inhibitory input seen by a motor unit has an invariant deterministic waveform, i.e., the neural encoding of the vestibular response can be treated as noise-free relative to the other sources of noise in the system. It is also assumed that that the inhibitory signal is only sensitive to the envelope of the stimulus. It is further assumed that that the processes that transform the stimulus envelope into the inhibitory signal are linear.

The spiking activity of a motor neuron can be described using a rate parameter. In general, this is the parameter that changes as the motor drive to the muscle is varied. Depending on the statistical model of the motor unit firing, there may be additional parameters required to completely describe the spiking activity. The manner in which the spike statistics are changed following inhibition depends on the motor neuron membrane properties. It is assumed that the effect of the inhibition on the spiking activity of a motor neuron is to modulate the rate parameter as a deterministic function of post-stimulus time. The inhibitory modulation of the spike rate can be further assumed to be a rectangular waveform defined by an inhibition duration and inhibition depth. Combined with the linearity assumption, this means that changes in the stimulus intensity are reflected as changes in the inhibition depth only, while the inhibition duration remains unchanged. Further, it is assumed that the duration of the inhibition can be estimated from measurements of extracellular compound potentials in SCM motor neurons. The amplitude of the MUAPr is assumed to be directly proportional to the number of fibers in the unit and the amplitude is assumed to be inversely proportional to the mean distance of the motor unit fibers to the electrodes. It is also assumed that all units evoke the same response waveform across the surface electrodes.

Referring to FIG. 9, the muscle model 910 is assumed to be an array of 250 motor units. This number is estimated from the EMG-based motor unit number estimates of human skeletal muscles and counts of spinal accessory motor neurons. The units differ from each other in their size (number of muscle fibers in the unit), and the distance to the electrodes of the electrical center of the unit. The number of fibers and the mean distance to of each unit electrodes contribute to the relative size of the surface potential generated by the unit. The surface response amplitude is assumed to be proportional to the number of units and inversely proportional to the unit depth. The size and depth of the motor unit specifies the relative amplitude of the motor unit response. The absolute amplitude depends on the amplitude of the surface response of a single action potential. In the example model shown in FIG. 9, the choice of this parameter determines the amplitude of the resulting surface EMG.

The recruitment model 905 translates the motor drive parameter into the firing rate of each unit. The motor drive K is a number between 0 and 100, representing the range of voluntary contraction effort, i.e., it corresponds to the percentage of the maximum voluntary contraction (% MVC). For example, at K=0, the firing rates of all units are zero, and at K=100, all the units have been recruited.

At the motor unit spiking model 915, a recruited motor unit fires in a quasi-periodic fashion, where the inter-spike interval (ISI) is Gaussian distributed about a mean value determined by the firing rate assigned to the unit. The firing probability (or firing rate) of a unit at a given time is computed by simulating the spike sequence of the unit over multiple independent trials and estimating the mean number of spikes in a sequence of narrow time bins. This estimate is a random process, and can be characterized by the mean rate at each time-bin and the correlations between the rates at different bins.

When the time axis is defined as the time duration following a given motor unit spike, we measured the post-spike firing probability (or a spike triggered average) for two units at two different values of motor drive. We saw that the mean rate is quasi-periodic with a periodicity equal to the mean ISI of the unit. The periodicity gets weaker with time, and disappears after roughly 5 cycles. The duration needed for the spike rate to become uniform is dependent on the standard deviation of the ISI distribution; in this simulation the standard deviation is ⅕th the mean ISI.

When the time axis is defined independently of the spiking activity, as is the case for a stimulus-triggered average, the averaged rate becomes independent of the post-stimulus time and the firing probability becomes uniform. In general, the nature of this process is non-white.

The surface EMG measures the response to the combined activity of all the units in the pool. These units fire independently of each other, and span a range of mean firing rates. In general, the variance of the firing rates is larger for the units whose mean rate is higher. The ratio of variance to mean is close to 1 for most motor units and over a wide range of mean firing rates, a property that is characteristic of a Poisson process.

For each trace, the spiking model 915 produces spike sequences for each of the active motor units $MU_1, MU_2, \ldots, MU_n$. The spike positions are encoded at a precision much greater than the sampling rate of the experimental and simulated surface EMG signals, to avoid introducing artificial correlations between spikes and spike trains.

The surface response model 920 models the surface response generated by a single motor unit action potential on the muscle. In this exemplary model, the response is modeled as the filter impulse response $h(t)$. This model assumes that the same waveform can be used to describe all the units, and that it is invariant with time and motor drive. In general, there is no direct means of measuring the surface response to a single action potential when the motor unit activity is driven by voluntary contraction effort. Therefore, in this model, $h(t)$ is determined as the sum of component waveforms derived from physiological models, but tailored to the characteristics of the surface EMG from individual subjects and sessions.

For each motor unit, each surface EMG trace is computed as the summation of individual spike responses $\Sigma Aa_i h(t-\tau_i)$, where each $h(t)$ is offset by a delay $\tau_i$ determined by the position of each motor unit spike, and is scaled by the response amplitude $a_i$ of the unit. The summation is taken over the (variable) number of spikes over a combined duration of the length of the trace and the length of $h(t)$. The spike positions $\tau_i$ as well as the $h(t)$ waveform are computed at a time resolution that is 10 times the sampling rate of the surface EMG. A set of 500 such simulated traces forms an ensemble, which corresponds to experimental traces recorded over a 40 second contraction.

From the above model components, surface EMG produced by the muscle for a given motor drive can be simulated considering the response characteristics specific to a particular subject and session.

Further as shown in FIG. 9, the spike inhibition model 925 describes the influence of the tone-burst stimulus on the spiking activity of the motor neurons. The stimulus is assumed to result in a fixed "internal response" that modulates the spike rate of the active motor units. This presumed internal response signal represents the response of the saccule, the neural coding and transformations that occur in the vestibular nuclei. Each motor unit is assumed to receive inhibitory projections of equal strength.

The modulation function is characterized by a duration T, which is fixed at 6 ms, and an inhibition depth D that takes values between 0 and 1. Once the spike positions for a particular motor unit are determined based on the spike's firing rate, the inhibition model deletes the spikes that fall within the interval T with a probability of deletion determined by the inhibition depth D. The thinned spike sequence is then passed to the surface response model to generate the motor unit's contribution to the surface EMG trace.

The inhibition depth can therefore be used to characterize a measure of the size of the internal response to the stimulus. In general, the inhibition depth reflects the stimulus intensity, as well as physiological characteristics of the peripheral vestibular system being modeled. The relationship between the stimulus intensity and the inhibition depth can therefore be used to provide information about the physiological state of the vestibular system. The model described in FIG. 9 can therefore be used to estimate the inhibition depth from experimentally recorded data.

The signal measured by the electrodes includes additive noise due to instrument sources as well as the electrical activity of muscles and nerves unrelated to the SCM that is being measured. This noise component is modeled in the simulation as zero-mean white Gaussian noise that is low-passed to a bandwidth of 1250 Hz with a 6th order Butterworth filter. The filter parameters are based on the noise signal recorded with no head turning and no acoustic stimulus. The filter bandwidth and the amplitude of the noise signal are set so that the spectrum of the simulated noise matches that of the experimental noise.

The inputs to the model included the inhibition depth D, motor drive K and the MUAPr waveform $h(t)$ computed for a particular subject and session. Each run of the model yielded a set of 500 synthetic EMG traces, corresponding to a recording duration of approximately 38.5 seconds. Each trace was an array of 1723 samples corresponding to the trace length of 77 ms sampled at 25 kHz, the same rate as the experimental recordings.

The three input parameters of the model were designed so that the statistical properties of the output traces match those of the experimentally recorded trace ensemble. The motor drive K and the MUAPr waveform $h(t)$ were designed to match the properties of the surface EMG. The inhibition depth D, was used to fit the properties of the VEMP.

The MUAPr response estimation module 930 used the assumption that the experimental surface EMG is the result of a white noise spiking process driving a linear filter with impulse response $h(t)$. $h(t)$ was therefore estimated for a particular subject/session from the power spectrum or the autocorrelation of the experimental data. The dimensionality of $h(t)$ was reduced to be a weighted sum of three "basis" functions, where each function was a Gaussian pulse that was scaled along the time axis, in amplitude, and shifted in position. Estimating $h(t)$ therefore reduced to choosing the amplitude, width and position of the three pulses such that the autocorrelation of the summed waveform matched the autocorrelation of the surface EMG. The amplitude and position of one of the pulses were fixed at nominal values of 1 and 0 respectively, leaving a total of 7 parameters to describe $h(t)$.

The parameter values were computed using a simple iterative search algorithm, to match the autocorrelation function of the experimentally recorded surface EMG signal from a given subject/session, subject to the constraint that h(t) integrates to zero.

The motor drive K was estimated using two parameters established by examining the synthetic EMG produced by the model at different values of motor drive. These parameters were the relationship between the variance or rms value of the EMG and the motor drive for different subjects/sessions, and the time interval over which the motor drive can assumed to be stationary. The latter was estimated by comparing the low-frequency components of the synthetic and the experimental EMG.

Using the model described in FIG. 9, a relationship between a parameter derived from measurements (such as the iCov) and a characteristic of a response signal (e.g., the inhibition depth) can be established. Such a relationship can then be used to estimate the characteristic from the measurements.

Results

Figures 10A, 10B:
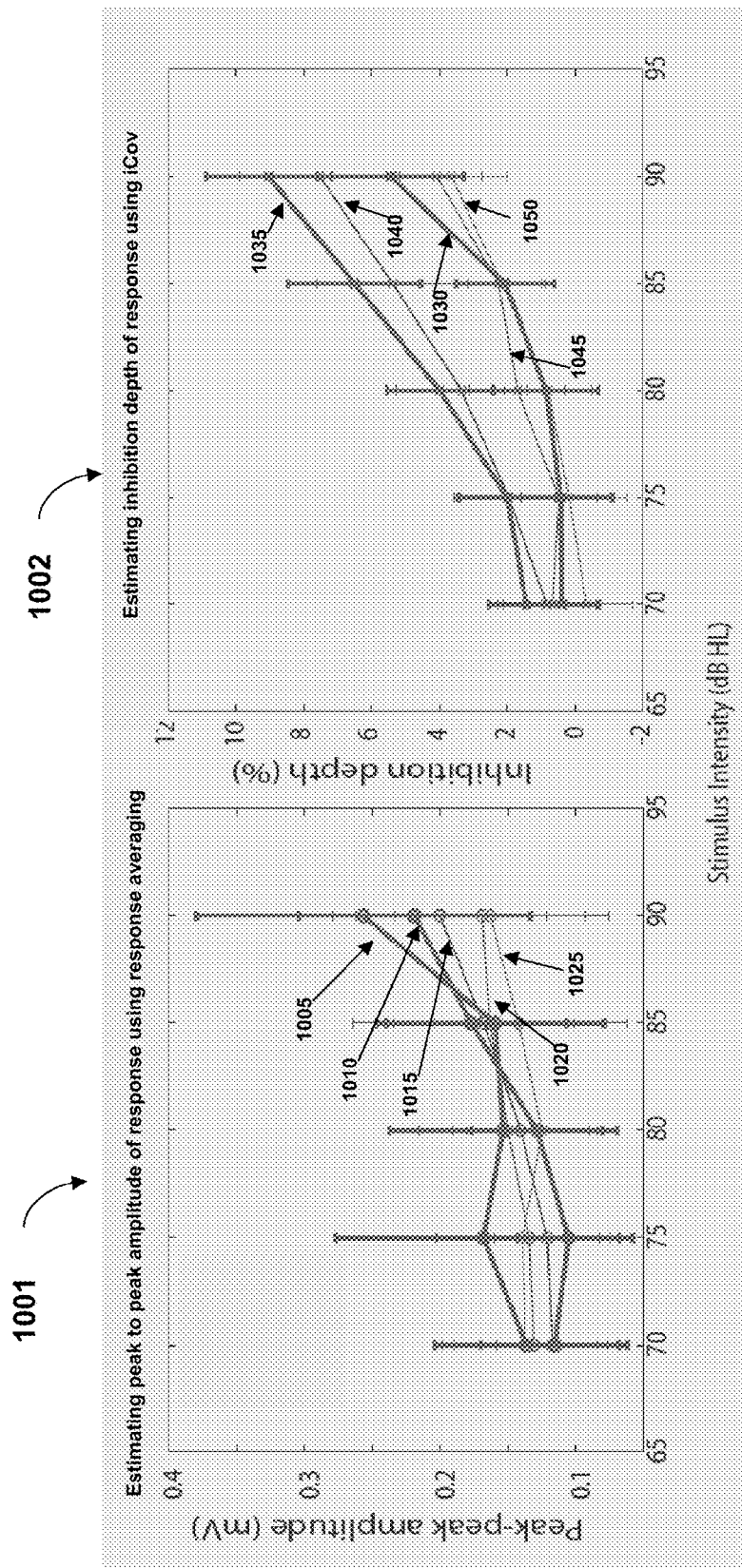
FIGS. 10A and 10B are plots showing results of analyses on measured VEMP signals.

Referring now to FIGS. 10A and 10B, the plots 1001 and 1002 illustrate the performance of the iCov metric for VEMP compared to the approach of averaging the response traces. Referring to FIG. 10A, the plot 1001 shows the curves 1005, 1010, 1015, 1020 and 1025, corresponding to 5 different subjects, respectively. In the response averaging approach, an average waveform is calculated from the traces in an ensemble and the peak to peak amplitude of the average waveform is measured as a predictor of a response to the stimulus signal. As seen from the plot 1001, for some subjects in this example, the peak to peak amplitude of the average response does not vary in a predictable fashion. For example, for the subject corresponding to the curve 1025, the peak to peak amplitude remains almost unchanged when the stimulus signal intensity is increased from 70 dB to 75 dB. Further, the peak to peak amplitude for curve 1025 goes down when the stimulus intensity is increased from 75 dB to 80 dB. This is not an expected phenomenon since the VEMP response, in general, should grow stronger with increased stimuli.

Referring now to FIG. 10B, the plot 1002 shows the results in case of estimating the inhibition depth using iCov for the same ensemble used in FIG. 10A. In the plot 1002, the curves 1030, 1035, 1040, 1045 and 1050 represent the same subjects, respectively, as in FIG. 10A. As seen from FIG. 10B, the inhibition depth, as estimated using the iCov, increases with increasing stimulus intensity for all subjects, which, in general, is the expected result.

Other Embodiments

It is to be understood that while the invention has been described in conjunction with the detailed description thereof, the foregoing description is intended to illustrate and not limit the scope of the invention, which is defined by the scope of the appended claims. The methods and systems described herein can be used for processing other signals, for example, where an underlying point process is modulated by a signal and a parameter of the modulation is to be estimated. Such signals arise in a wide variety of fields including seismology, neurophysiology, water-flow modeling and optical detection, and are within the scope of this application. Other aspects, advantages, and modifications are within the scope of the following claims.

What is claimed is:

1. A method for estimating a response of at least a part of a physiological system to a first deterministic stimulus signal, the method comprising:

receiving, at a computing device, a first signal measured from the physiological system in response to the first stimulus signal;

separating, using a processor, the measured first signal into a plurality of segments, each segment representing a response of the physiological system to a corresponding portion of the first stimulus signal;

generating, using a processor, a template signal representing the plurality of segments;

calculating, using a processor, a measure of similarity of each segment in the plurality of segments to the template signal to provide a set of scalar quantities, wherein calculating the measure of similarity comprises calculating a correlation between the segment and the template signal; and determining, using a processor, a metric representing a characteristic of the response of at least a part of the physiological system to the first stimulus signal, wherein the metric is a ratio of a measure of central tendency to a measure of dispersion, wherein the measure of central tendency and the measure of dispersion are computed from the set of scalar quantities.

2. The method of claim 1, further comprising measuring the first signal from the physiological system using one or more electrodes.

3. The method of claim 1, wherein each segment is substantially equal in duration to other segments in the plurality of segments.

4. The method of claim 1, wherein each segment is substantially equal in length to a corresponding portion of the stimulus signal.

5. The method of claim 1, further comprising generating the template signal by averaging the segments.

6. The method of claim 1, further comprising:

receiving, at a computing device, a second signal measured from the physiological system in response to a second deterministic stimulus signal, an intensity of which is greater than the intensity of the first stimulus signal;

separating, using a processor, the measured second signal into a plurality of segments, each segment representing a response of the physiological system to a corresponding portion of the second stimulus signal; and generating the template signal based on the plurality of segments from the second measured signal.

7. The method of claim 6, wherein the second signal is measured under substantially the same measurement conditions as for the first signal.

8. The method of claim 1, further comprising:

receiving, at a computing device, a plurality of third signals measured from a plurality of physiological systems of substantially same type in a population of subjects in response to a third deterministic stimulus signal;

separating, using a processor, each of the plurality of third signals into a plurality of segments, each segment representing a response of the corresponding physiological system to a corresponding portion of the third stimulus signal; and generating the template signal based on the segments from the plurality of third signals.

9. The method of claim 8, wherein the plurality of third signals are each measured under substantially the same measurement conditions as for the first signal.

10. The method of claim 1, wherein the template signal is calculated based on one or more parameters of a theoretical model of the physiological system.

11. The method of claim 1, wherein the set of scalar quantities includes at least one of a correlation coefficient, an inner product, a sum of squared differences (SSD), a root mean squared difference (RMSD), a sum of absolute differences (SAD), and mutual information.

12. The method of claim 1, wherein the measure of central tendency is a mean and the measure of dispersion is a standard deviation.

13. The method of claim 1, wherein the physiological system is a vestibular system, the first signal is a vestibular evoked myogenic potential (VEMP), and the stimulus signal is an acoustic signal.

14. The method of claim 13, further comprising providing instructions to a subject to control a body part of the subject in accordance with the stimulus signal, wherein the physiological system is a part of the subject.

15. The method of claim 1, wherein the stimulus signal is one or more of an acoustic signal, an electrical signal, a visual signal, and a mechanical signal.

16. The method of claim 1, wherein the first signal is measured in the presence of a random process and the response of at least a part of the physiological system to the stimulus signal modulates the random process.

17. The method of claim 13, wherein the response of at least a part of the vestibular system to the acoustic signal inhibits a spiking activity of a muscle and a level of the spiking activity is represented by the characteristic.

18. The method of claim 17, wherein the first signal is measured in the presence of concomitant physiological noise and the response of at least a part of the vestibular system to the acoustic signal modulates the physiological noise, and wherein an extent of the modulation depends on the level of spiking activity.

19. The method of claim 1, further comprising applying the first stimulus signal to the physiological system.

20. The method of claim 6, further comprising applying the second stimulus signal to the physiological system.

21. A system for estimating a response of at least a part of a physiological system to a first stimulus signal, the system comprising:
   a processor for:
      separating a first signal into a plurality of segments, each segment representing a response of the physiological system to a corresponding portion of the first stimulus signal, wherein the first signal is measured from the physiological system in response to the first stimulus signal,
      generating a template signal representing the plurality of segments,
      calculating a measure of similarity of each segment in the plurality of segments to the template signal to provide a set of scalar quantities, wherein calculating the measure of similarity comprises calculating a correlation between the segment and the template signal, and
      determining a metric representing a characteristic of the response of at least a part of the physiological system to the first stimulus signal, wherein the metric is a ratio of a measure of central tendency to a measure of dispersion, wherein the measure of central tendency and the measure of dispersion are computed from the set of scalar quantities; and
   a device for measuring the first signal.

22. The system of claim 21, wherein the device comprises one or more electrodes.

23. The system of claim 21, further comprising an audio device for providing the stimulus as an acoustic signal, wherein the physiological system is a vestibular system and the first signal is a vestibular evoked myogenic potential (VEMP).

24. The system of claim 23, wherein the response of at least a part of the vestibular system to the acoustic signal inhibits a spiking activity of a muscle, a level of the spiking activity being represented by the characteristic.

25. The system of claim 24, wherein the first signal is measured in the presence of concomitant physiological noise and the response of at least a part of the vestibular system to the acoustic signal modulates the physiological noise, wherein an extent of modulation depends on the level of spiking activity.

26. A computer-readable medium storing a computer program for estimating a response of at least a part of a physiological system to a first deterministic stimulus signal, the computer program comprising instructions for causing a computer system to:
   receive a first signal measured from the physiological system in response to the first stimulus signal;
   separate the measured first signal into a plurality of segments, each segment representing a response of the physiological system to a corresponding portion of the first stimulus signal;
   generate a template signal representing the plurality of segments;
   calculate a measure of similarity of each segment in the plurality of segments to the template signal to provide a set of scalar quantities, wherein calculating the measure of similarity comprises calculating a correlation between the segment and the template signal; and
   determine a metric representing a characteristic of the response of at least a part of the physiological system to the first stimulus signal, wherein the metric is a ratio of a measure of central tendency to a measure of dispersion, wherein the measure of central tendency and the measure of dispersion are computed from the set of scalar quantities.

27. A method for estimating a response of at least a part of a physiological system to a first deterministic stimulus signal, the method comprising:
   receiving, at a computing device, a first signal measured from the physiological system in response to the first stimulus signal;
   separating, using a processor, the measured first signal into a plurality of segments, each segment representing a response of the physiological system to a corresponding portion of the first stimulus signal;
   generating, using a processor, a template signal representing the plurality of segments, wherein the template signal is generated based on one or more parameters of a theoretical model of the physiological system;
   calculating, using a processor, a measure of similarity of each segment in the plurality of segments to the template signal to provide a set of scalar quantities; and
   determining, using a processor, a metric representing a characteristic of the response of at least a part of the physiological system to the first stimulus signal, wherein the metric is a ratio of a measure of central tendency to a measure of dispersion, wherein the measure of central tendency and the measure of dispersion are computed from the set of scalar quantities.

28. The method of claim 27, further comprising measuring the first signal from the physiological system using one or more electrodes.

29. The method of claim 27, wherein each segment is substantially equal in duration to other segments in the plurality of segments.

30. The method of claim 27, wherein each segment is substantially equal in length to a corresponding portion of the stimulus signal.

31. The method of claim 27, wherein the set of scalar quantities includes at least one of a correlation coefficient, an inner product, a sum of squared differences (SSD), a root mean squared difference (RMSD), a sum of absolute differences (SAD), and mutual information.

32. The method of claim 27, wherein the measure of central tendency is a mean and the measure of dispersion is a standard deviation.

33. The method of claim 27, wherein the physiological system is a vestibular system, the first signal is a vestibular evoked myogenic potential (VEMP), and the stimulus signal is an acoustic signal.

34. The method of claim 33, further comprising providing instructions to a subject to control a body part of the subject in accordance with the stimulus signal, wherein the physiological system is a part of the subject.

35. The method of claim 27, wherein the first signal is measured in the presence of a random process and the response of at least a part of the physiological system to the stimulus signal modulates the random process.

36. The method of claim 33, wherein the response of at least a part of the vestibular system to the acoustic signal inhibits a spiking activity of a muscle and a level of the spiking activity is represented by the characteristic.

37. The method of claim 36, wherein the first signal is measured in the presence of concomitant physiological noise and the response of at least a part of the vestibular system to the acoustic signal modulates the physiological noise, and wherein an extent of the modulation depends on the level of spiking activity.

38. A system for estimating a response of at least a part of a physiological system to a first stimulus signal, the system comprising:
    a processor for:
        separating a first signal into a plurality of segments, each segment representing a response of the physiological system to a corresponding portion of the first stimulus signal, wherein the first signal is measured from the physiological system in response to the first stimulus signal,
        generating a template signal representing the plurality of segments, wherein the template signal is generated based on one or more parameters of a theoretical model of the physiological system,
        calculating a measure of similarity of each segment in the plurality of segments to the template signal to provide a set of scalar quantities, and
        determining a metric representing a characteristic of the response of at least a part of the physiological system to the first stimulus signal, wherein the metric is a ratio of a measure of central tendency to a measure of dispersion, wherein the measure of central tendency and the measure of dispersion are computed from the set of scalar quantities; and
    a device for measuring the first signal.

39. The system of claim 38, wherein the device comprises one or more electrodes.

40. The system of claim 38, further comprising an audio device for providing the stimulus as an acoustic signal, wherein the physiological system is a vestibular system and the first signal is a vestibular evoked myogenic potential (VEMP).

41. The system of claim 40, wherein the response of at least a part of the vestibular system to the acoustic signal inhibits a spiking activity of a muscle, a level of the spiking activity being represented by the characteristic.

42. The system of claim 41, wherein the first signal is measured in the presence of concomitant physiological noise and the response of at least a part of the vestibular system to the acoustic signal modulates the physiological noise, wherein an extent of modulation depends on the level of spiking activity.

43. A computer-readable medium storing a computer program for estimating a response of at least a part of a physiological system to a first deterministic stimulus signal, the computer program comprising instructions for causing a computer system to:
    receive a first signal measured from the physiological system in response to the first stimulus signal;
    separate the measured first signal into a plurality of segments, each segment representing a response of the physiological system to a corresponding portion of the first stimulus signal;
    generate a template signal representing the plurality of segments, wherein the template signal is generated based on one or more parameters of a theoretical model of the physiological system;
    calculate a measure of similarity of each segment in the plurality of segments to the template signal to provide a set of scalar quantities; and
    determine a metric representing a characteristic of the response of at least a part of the physiological system to the first stimulus signal, wherein the metric is a ratio of a measure of central tendency to a measure of dispersion, wherein the measure of central tendency and the measure of dispersion are computed from the set of scalar quantities.

* * * * *